(12) United States Patent
Alexandre et al.

(10) Patent No.: US 6,758,829 B2
(45) Date of Patent: Jul. 6, 2004

(54) NEEDLELESS SYRINGE FUNCTIONING WITH A DOUBLE-COMPOSITION PYROTECHNIC CHARGE

(75) Inventors: Patrick Alexandre, Gray (FR); Patrick Cognot, Le Mee sur Seine (FR); Joel Lafforgue, Itteville (FR); Denis Roller, La Ferte Alais (FR)

(73) Assignee: Crossject, Paris (FR)

( * ) Notice: Subject to any disclaimer, the term of this patent is extended or adjusted under 35 U.S.C. 154(b) by 68 days.

(21) Appl. No.: 10/221,965

(22) PCT Filed: Mar. 27, 2001

(86) PCT No.: PCT/FR01/00921

§ 371 (c)(1),
(2), (4) Date: Oct. 16, 2002

(87) PCT Pub. No.: WO01/78810

PCT Pub. Date: Oct. 25, 2001

(65) Prior Publication Data

US 2003/0135155 A1 Jul. 17, 2003

(30) Foreign Application Priority Data

Apr. 19, 2000 (FR) .............................. 00 05031

(51) Int. Cl.⁷ .............................................. A61M 5/30
(52) U.S. Cl. ........................................ 604/69; 604/68
(58) Field of Search ....................... 604/68, 69, 70, 604/71, 72, 73, 131, 140, 141, 143, 145, 187

(56) References Cited

U.S. PATENT DOCUMENTS

| 2,322,244 A | 6/1943 | Lockhart et al. |
| 2,704,542 A | 3/1955 | Scherer et al. |
| 3,802,430 A | 4/1974 | Schwebel et al. |
| 3,945,379 A | 3/1976 | Pritz et al. |
| 4,059,107 A | 11/1977 | Iriguchi et al. |
| 4,089,334 A | * 5/1978 | Schwebel et al. ............. 604/69 |
| 4,124,024 A | 11/1978 | Schwebel et al. |
| 5,383,851 A | 1/1995 | McKinnon, Jr. et al. |
| 5,399,163 A | 3/1995 | Peterson et al. |
| 5,520,639 A | 5/1996 | Peterson et al. |
| 6,080,248 A | 6/2000 | Finck et al. |
| 6,258,063 B1 | 7/2001 | Haar et al. |
| 6,537,245 B1 | * 3/2003 | Alexandre et al. ............. 604/69 |
| 6,610,028 B1 | * 8/2003 | Alexandre et al. ............. 604/69 |
| 2002/0151842 A1 | 10/2002 | Gonnelli et al. |
| 2002/0156418 A1 | 10/2002 | Gonnelli et al. |
| 2002/0161329 A1 | 10/2002 | Gonnelli et al. |

FOREIGN PATENT DOCUMENTS

| WO | WO 98/31409 | 7/1998 |
| WO | WO 99/22790 | 5/1999 |
| WO | WO 00/44421 A1 | 8/2000 |

* cited by examiner

*Primary Examiner*—Brian L. Casler
*Assistant Examiner*—Mark K Han
(74) *Attorney, Agent, or Firm*—Oliff & Berridge, PLC

(57) ABSTRACT

The technical field of the invention is that of pre-filled and disposable needleless syringes, used for intradermal, subcutaneous and intramuscular injections of liquid active principle for therapeutic use in human and veterinary medicine. The inventive syringes (1) are mainly characterised in that they function with a pyrotechnic charge (6) consisting of a mixture of powder with high burning rate and a powder with low burning rate. Indeed, the combustion of the powder with a high burning rate enables to communicate instantly, through a piston (3), a very high speed to the active principle (4), whereas the combustion of the powder with a low burning rate enables to maintain a threshold pressure level to proceed with the injection, so as to ensure that the active principle (4) penetrates through the skin. Thus, the injection is properly and homogeneously without any loss of active liquid (4).

17 Claims, 1 Drawing Sheet

NEEDLELESS SYRINGE FUNCTIONING WITH A DOUBLE-COMPOSITION PYROTECHNIC CHARGE

Figure 2:
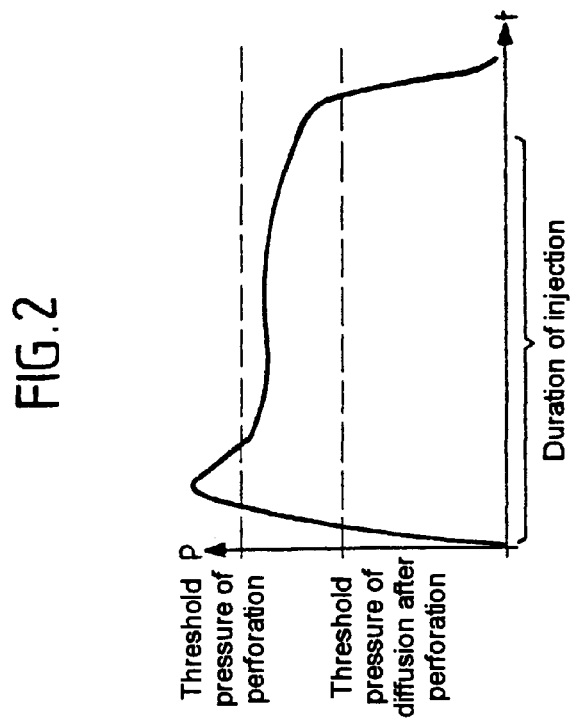

The technical field of the invention is that of prefilled and disposable needleless syringes functioning with a gas generator and used for intradermal, subcutaneous and intramuscular injections of liquid active principle for therapeutic use in human or veterinary medicine.

For the injection devices according to the invention, a liquid active principle consists of a more or less viscous liquid, or a mixture of liquid, or a gel. The active principle can be a solid dissolved in a suitable solvent for injection. It can also be represented by a powdered solid in more or less concentrated suspension in a suitable liquid. The particle size of the principle must be compatible with the diameter of the conduits in order to avoid blockages.

The needleless syringes according to the invention have the particular feature of functioning with a pyrotechnic gas generator which involves a pyrotechnic charge consisting of the mixture of two powders, the main benefit of this being to control, over the course of time, the pressure of the liquid active principle as it leaves the nozzle, in such a way that each phase of the injection is effected under the required conditions.

In the field of needleless syringes for injection of liquid active principles, it transpires that there is no patent relating to the use of a pyrotechnic gas generator involving the mixture of two powders. By contrast, the use of a single pyrotechnic charge for this type of syringe already exists and is the subject of several patents. By way of example, mention may be made of the patent U.S. Pat. No. 2,322,244 which relates to a hypodermic needleless injector functioning with a blank cartridge. The liquid to be injected, placed in contact with the cartridge, is expelled from the injector under the effect of the pressure generated by the combustion gases. Another patent, WO 98/31409, describes a hypodermic injection system involving a pyrotechnic charge which consists of an explosive or a powder. The specific feature of this injector is that it is designed to attempt to control the problems associated with the kinetics of expulsion of the liquid active principle, not by acting on the characteristics of the pyrotechnic composition, but by having a specific geometry defining in particular an adjoining gas expansion chamber which is provided with a vent. The pyrotechnic charge, which is located in immediate proximity to the liquid active principle, acts directly and instantaneously on said principle by giving it a very high initial speed, while the gases invade the main chamber and the adjoining chamber. The pressure exerted on the active principle then decreases and eventually fixes at an almost constant value, which is sufficient to cause it to penetrate the patient's skin. The adjoining chamber makes it possible to regulate this pressure. Finally, the patent U.S. Pat. No. 2,704,542 relates to a method of injection by liquid jet. This method does not specifically involve a pyrotechnic charge but uses a device intended to control the pressure profiles. In this case, the method used to achieve this objective is based on the two-stage sliding movement of a two-part piston formed by a central cylinder of small cross section housed in a hollow cylinder. An upstream pressure first causes a displacement of low amplitude of the central cylinder in order to communicate a brief but very intense impulse to the liquid which is to be expelled, then the whole of the piston displaces in order to continue to expel said liquid at the appropriate pressure, so as to ensure proper penetration.

The needleless syringes according to the invention are designed to ensure penetration, through the skin, of all of the liquid active principle, without causing any losses of said liquid on account of insufficient speed, since said losses could prove to be detrimental to the quality of the injection. The method used to control the pressure of the liquid, as a function of time, at the nozzle outlet lies in using a pyrotechnic charge consisting of the mixture of two powders, one called "fast-burning" and the other called "slow-burning", the dimensional and chemical characteristics of these two powders being conditioned by the geometry and dimensions of the syringes, and also by the injection system including the reservoir of liquid active principle, if appropriate a piston for thrusting said active principle, and a nozzle comprising expulsion orifices. The fast-burning powder, when combusted, has the main function of communicating almost instantaneously to the liquid active principle a level of pressure such that the latter instantaneously acquires a speed of several hundreds of meters per second, allowing it to penetrate the patient's skin as it is expelled from the syringe. The slow-burning powder, which is combusted simultaneously, is able to guarantee the active principle a minimum level of pressure throughout the duration of the injection and sufficient to continue the diffusion through the orifice created in the skin by the effect of the fast-burning powder. The concepts of fast-burning powder and slow-burning powder will be explained later.

Thus, the needleless syringes according to the invention, while retaining their geometry and their reduced size, make it possible to ensure reliable and correct injection, in contrast to the injection devices described in the prior art, and in which the search for an optimized pressure profile involves a modification of their structure, illustrated by the addition of supplementary parts or attached volumes, thereby increasing their size and making the mechanism of their functioning more complex.

Moreover, irrespective of the syringe configuration, which may be dictated by imperatives linked to the specificity of an injection, it is still possible to determine a mixture of powders suitable for ensuring a satisfactory injection without in any way having to modify said syringe. This is because the liquid active principle can be present in a greater or lesser quantity, in more or less viscous form, in a syringe of linear or compact architecture. The powder mixture will be defined taking into consideration all of these constraints.

The needleless syringes according to the invention ensure correct and reliable injection and permit a very high degree of flexibility of use on account of the great variability of the pyrotechnic charges which can be used for the mixture, and all this without adding to their size.

The subject of the present invention is a needleless syringe comprising, in succession, a pyrotechnic gas generator, at least one piston, a reserve of liquid active principle, and an ejection nozzle, characterized in that the pyrotechnic gas generator comprises a pyrotechnic charge consisting of the mixture of at least two powders.

The pyrotechnic charge preferably consists of the mixture of a first powder and of a second powder.

The powders are characterized, on the one hand, by their chemical formulation and, on the other hand, by their geometry. The chemical formulation integrates all of the components included in the powder and to which there must be added a weighting coefficient corresponding to the fraction by mass of said component. The geometry of the powder reflects the geometry of each particle which it comprises. A particle is defined by its shape, its dimensions and the number of holes it has, said holes contributing to determining a burning thickness.

When it is stated that the pyrotechnic charge consists of the mixture of a first powder and of a second powder, this signifies that the two powders are different from one another and that this difference may lie in only one of the parameters mentioned above. In other words, the two powders can, for example, have the same chemical composition but have particles of slightly different geometry.

The pyrotechnic charge advantageously consists of a mixture of two powders in loose form, that is to say the two powders are in a state in which the particles are mixed haphazardly, without any particular order, the resulting powder matching the shape of the container in which it is located, while forming interstices between the particles. However, it is also conceivable to envision at least one of the two powders being in an ordered or specific form, for example in the form of a bundle of strands or in the form of a single particle of considerable size, or even in agglomerated form.

According to another preferred variant of the invention, the pyrotechnic charge consists of the mixture of two powders which are each in the form of a compact block, and said blocks can either be in contact and in continuity with one another or can be concentric in order to define just a single block having in its central part the composition of the first powder and in its peripheral part the composition of the second powder, or vice versa depending on the ignition sequence.

The first powder preferably has a dynamic vivacity of greater than 8 $(MPa.s)^{-1}$.

The second powder advantageously has a dynamic vivacity which is less than 16 $(Mpa.s)^{-1}$ and which is systematically less than that of the first powder.

This is in fact the value of the dynamic vivacity of a powder particle at half combustion. The dynamic vivacity is a parameter which reflects the vivacity of a powder throughout combustion.

It is given by the formula:

$$L(z) \frac{1}{P} \cdot \frac{1}{P\max} \cdot \frac{(dP)}{dt}$$

where P is the instantaneous pressure corresponding to the state of advance z.

Pmax is the maximum pressure reached.

dP/dt is the derivative of the pressure with respect to time $$z = \frac{P}{P\max}.$$

The conditions in which the values of the dynamic vivacity were obtained are the following:
 this is the value of the dynamic vivacity at half combustion, that is to say the value corresponding to z=0.5,
 the values were obtained for firing in a manometric chamber having a chamber volume of 27.8 $cm^3$,
 the charging density is 0.036 $g/cm^3$,
 the powder mass is 1 g.

For the needleless syringes according to the invention, the pyrotechnic charge consists of the mixture of a powder with a high vivacity and a powder with a lower vivacity, hence the terms fast-burning powder and slow-burning powder. The powder with the high vivacity ensures a rapid pressure increase of the order of 1 ms, while the powder with the low vivacity makes it possible to continue the production of gas during the injection in order to compensate for the drop in pressure due to the increase in the volume of the combustion chamber, caused by the displacement of the piston, and also to compensate for the heat losses at the walls, for 4 to 8 ms. The use of two powders of different vivacity also results in a decrease in the maximum pressure of functioning, by which means it is possible to reduce the mechanical strength of the device and consequently the production costs. Indeed, if the pyrotechnic charge were to consist only of a single fast-burning powder, the pressure profile in the liquid active principle would resemble that of a pure release.

To ensure that the pressure at the end of injection is not less than the threshold injection pressure below which the liquid no longer correctly penetrates the tissues, it would be necessary to increase the maximum pressure in order to offset the preceding profile upward, so that during the entire injection the injection pressure always remains higher than the threshold pressure. By using a mixture of two powders of different vivacity, it is possible to maintain the injection pressure above the threshold value without thereby having to increase the maximum pressure.

The rapid rise in pressure at the start of injection is necessary to ensure good penetration into the skin without escape of active principle.

The thrust of the liquid active principle is preferably ensured by a single piston which transmits to the liquid the pressure prevailing in the gas expansion chamber, reducing its intensity but maintaining the general profile of its variation as a function of time. More generally, the pyrotechnic charge can be adapted to the number of pistons involved in the thrusting of the liquid active principle, to their shape, to their nature, and to the geometry of the nozzle and the number of holes which it possesses. Since a powder is characterized by numerous chemical and structural parameters, the mixture of two powders offers an almost unlimited number of combinations which can satisfy any type of situation.

At least one of the two powders is advantageously based on nitrocellulose, the content by mass of which is between 0.45 and 0.99. The content by mass of a component is characterized as being the ratio of the mass of this component to the total mass of all the components. The content by mass of nitrocellulose is advantageously between 0.93 and 0.98.

Because of their specific properties, the nitrocelluloses represent the essential basis of the powders presently used for the propulsion of bullets, shells or various projectiles in tube weapons. According to a first embodiment of the invention, each powder which is based on nitrocellulose also contains a nitric ester, for example nitroglycerin. For the powders containing these two components, the content by mass of nitrocellulose is preferably between 0.49 and 0.61 and the content by mass of nitroglycerin between 0.35 and 0.49. The first powder is advantageously chosen from among porous powders. The first powder which is porous preferably contains nitrocellulose, and the content by mass of nitrocellulose is between 0.93 and 0.98. A powder based on nitrocellulose is rendered porous by incorporation, during the mixing phase of their manufacturing process, of a salt such as potassium nitrate which is then removed by dissolution. The potassium nitrate crystals remaining incorporated at the surface of the powder particles constitute hot spots under the influence of an igniter. A porous surface thus makes it possible, inter alia, to improve the ignition of the powder.

The first powder advantageously has a burning thickness of less than or equal to 0.5 mm. The burning thickness corresponds to the smallest dimension of the powder particle on which the combustion front will progress then stop, thus making it possible to fix the combustion time of said particle. As a powder particle burns on all its faces at the same time, the burning thickness corresponds to half its smallest thickness. This burning thickness depends on the shape of the particle, its dimensions, and the number and position of the holes which it possesses.

The particles constituting the powders which can be mixed to form a pyrotechnic charge in accordance with that used for needleless syringes according to the invention can be in various forms. For example, they can be monotubular, multitubular, spherical, crushed spherical, cylindrical, or can be in the form of flakes or sticks. For each of these geometries, the burning thickness represents a perfectly identified parameter.

For example:

for a spherical particle, the burning thickness corresponds to the radius of the particle, for a cylindrical particle, of considerable length, the burning thickness corresponds to the radius of the particle, for a monotubular particle, the burning thickness corresponds to half the thickness of the particle taken along a radial direction, for a multitubular particle for which the holes are regularly spaced from one another, the burning thickness corresponds to half the length separating two successive holes.

It is particularly recommended to choose, as fast-burning powder, a powder having a low burning thickness. The fast-burning powder is advantageously porous and based on nitrocellulose. It advantageously has a burning thickness equal to 0.3 mm and is in the form of sticks or flakes.

The first powder preferably has a combustion time of less than 6 milliseconds. This is a time corresponding to a real situation, that is to say a "syringe" configuration entailing the following conditions:

powder combustion takes place in a chamber whose final volume is 1.6 cm$^3$, the thrust of the liquid is provided for by a component formed by a piston.

The second powder preferably has a burning thickness of between 0.1 mm and 1 mm.

Figure 1:
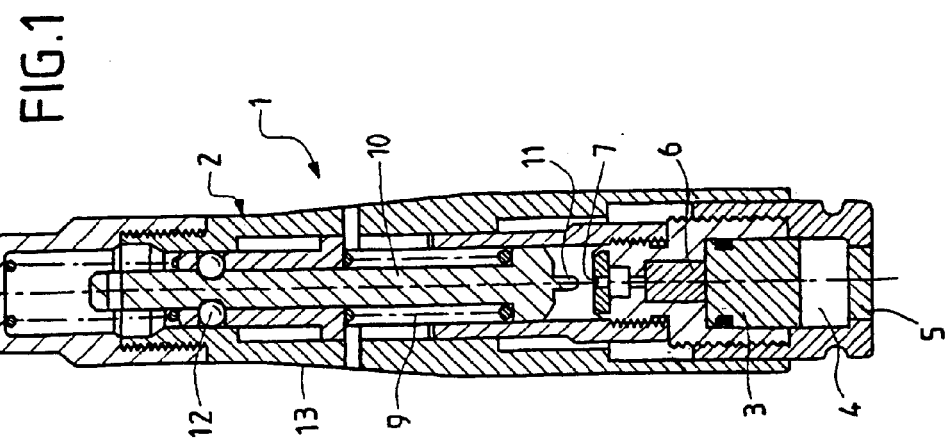

The second powder advantageously has a combustion time which is greater than 4 ms and which is systematically greater than that of the first powder. The combustion time of the second powder was obtained under the same conditions as those in which that of the first powder was determined. The combustion time of the second powder must always exceed that of the first powder, since the second powder is present in the mixture only to make up for the lack of pressure observed upon combustion of the first powder alone. The combustion times of the two powders are linked to the specificity of the injection and in particular to the association between the volume of active principle to be injected and the characteristics of the nozzle bearing essentially on the number of evacuation channels, their distribution and their diameter. According to a preferred embodiment of the invention, the total mass of the two powders is less than 100 mg. This threshold limit is dictated, on the one hand, by the imperatives linked to the injection, requiring in particular a speed of the liquid on impact on the skin of between 100 m/s and 200 m/s, and, on the other hand, to the dimensions of the needleless syringe which have to be compatible with those of an object of small size and which is light and manageable. The ratio of the mass of the first powder to the total mass of the two powders is advantageously greater than 0.1. The fact that the characteristics of the initial impulse must communicate a very high speed instantaneously to the liquid active principle necessitates a minimum quantity of powder, which cannot be less than 10% of the total mass of the powder.

According to a first preferred variant of the invention, the shape function of the second powder is progressive. The shape function of a powder in fact is based on the shape function of a particle from which it is made up, assuming all the particles are identical. The shape function of a particle is given by the ratio S/So where So is the surface of initial combustion of the particle and S is its surface of combustion at a given state of advance of said combustion. This shape function reflects the development of the surface of combustion of a particle as a function of time during the combustion. For a given powder, the greater the combustion surface, the greater the quantity of gas released per unit of time and the more rapid the rise in pressure in a closed volume. When the piston is displaced at the start of injection, the volume of the combustion chamber increases progressively, and, with a view to maintaining a substantially constant pressure level in said increasing volume, it is desirable to use a second, slow-burning powder with a progressive shape function.

According to a second preferred variant of the invention, the shape function of the second powder is almost constant. The reason is that under certain conditions, and in particular depending on the nature of the first, fast-burning powder used, a second, slow-burning powder having a constant shape function may suffice. As the shape function depends essentially on the geometry of the powder particle, the particles of the second, slow-burning powder will thus preferably have a multitubular shape or monotubular shape for which the shape functions are respectively progressive and almost constant.

The multitubular powders will preferably have three holes, seven holes or nineteen holes depending on the pressure profile sought.

The pyrotechnic gas generator advantageously comprises a device for initiation of the pyrotechnic charge, involving a percussion device and a primer. It is also possible to use an initiation system based on a piezoelectric crystal or a roughened surface.

The needleless syringes according to the invention have the advantage of guaranteeing a satisfactory injection of all of the liquid active principle, while retaining a simple mechanism of functioning and a reduced size which require neither the provision of specific components, which are sources of additional machining and additional costs, nor any in-depth modification in the geometry of the body of said syringes.

Moreover, with the great variability of the pyrotechnic compositions which can be used for the mixtures, it is possible to obtain a very great variety of pressure profiles which can be adapted to all the possible configurations. Finally, the perfect control of the effects generated by the combustion of a pyrotechnic charge combined with largely proven firing systems gives the needleless syringes according to the invention a character of great reliability and safety.

The following nonlimiting examples illustrate the invention, with reference being made to FIGS. 1 and 2.

FIG. 1 is a view showing a longitudinal axial cross section through a needleless syringe according to the invention.

FIG. 2 is a simplified typical graph showing the variation in pressure in the liquid as a function of time, generated by the combustion of a double-composition charge in a syringe according to the invention.

Referring to FIG. 1, a needleless syringe 1 according to the invention comprises a pyrotechnic gas generator 2, a piston 3, a reservoir of liquid active principle 4, and an ejection nozzle 5. The terms "injection nozzle" and "ejection nozzle" are equivalent.

The pyrotechnic gas generator 2 comprises a device for initiation of a pyrotechnic charge 6, involving a percussion device and a primer 7. The percussion device which is triggered by a push button 8 comprises a prestressed spring 9 and an elongate weight 10 provided with a striker pin 11. The weight 10 is blocked by at least one retaining ball 12 wedged between said weight 10 and a hollow cylindrical body 13 in which said weight 10 can move. The primer 7 and the pyrotechnic charge 6, of substantially cylindrical shape, are housed in the hollow cylindrical body 13, downstream of the weight 10. The pyrotechnic charge 6 opens into a widened space, of substantially cylindrical shape, occupied in its upstream part by the piston 3 and in its downstream part by the reservoir of liquid active principle 4, said widened space being closed off at its end by the ejection nozzle 5 which is provided with several channels bringing the active principle 4 and the outside of the syringe 1 into communication. These various elements are mutually arranged in such a way that they are in continuity with one another, the pyrotechnic charge 6 being in contact with the piston 3, itself in contact with the liquid active principle 4, itself delimited by the nozzle 5. In order to avoid the liquid active principle 4 escaping from the syringe 1, a stopper is fixed at the level of the nozzle 5 and obstructs its channels, said stopper being withdrawn before use. The pyrotechnic charge 6 consists of the mixture of two loose powders.

The method of functioning of a needleless syringe 1 according to the invention is as follows.

The user positions the syringe 1 in such a way that the nozzle 5 bears against the skin of the patient to be treated. A pressure applied to the push button 8 allows the hollow cylindrical body 13 to move until its widened part is situated opposite the retaining ball 12. The ball 12 escapes from its seat, thereby freeing the weight 10, which, subjected to the action of the spring 9 which releases, is abruptly accelerated toward the primer 7, with the striker pin 11 leading. The reaction of the primer 7 results in the firing of the pyrotechnic charge 6 which decomposes and emits gases.

Referring to FIG. 2, the fast-burning powder then communicates to the piston 3 a high initial speed of displacement so that the liquid active principle 4, as soon as it leaves the nozzle 5, can immediately be driven at a sufficiently high speed to penetrate the skin. The slow-burning powder maintains, within the liquid active principle 4, a threshold pressure level allowing it, for the continuation of the injection, to preserve its power of diffusion through the skin, once the latter has been perforated. In this way, the injection takes place correctly and without any loss of liquid active principle 4.

The following nonlimiting examples illustrate the main feature of the invention, which relates to the pyrotechnic charge 6.

EXAMPLE 1

The tables below recapitulate the principal characteristics of the two powders used for the first mixture.

| I - Chemical composition | |
|---|---|
| COMPONENTS | Fraction by mass ×100 |
| Fast-burning powder | |
| Nitrocellulose | 93.0 |
| Dinitrotoluene | 2.0 |
| Dibutylphthalate | 1.2 |
| Diphenylamine | 1.0 |
| Graphite | 0.5 |
| Residual solvent | 0.2 |
| Residual salt | 0.4 |
| Humidity | 1.2 |
| Colorant | Traces |
| Slow-burning powder | |
| Nitrocellulose | 95 |
| Additives | 5 |

| II - Structural characteristics and parameters associated with combustion | | | | | | |
|---|---|---|---|---|---|---|
| | Porosity | Combustion time (ms) | Dynamic vivacity at half combustion $(MPa \cdot s)^{-1}$ | Burning thickness (mm) | Shape of particles | Shape function |
| Fast-burning powder | YES | 0.8 | 24 | 0.2–0.5 | flake | degressive |
| Slow-burning powder | NO | 3.1 | 11 | 0.22 | monotubular | almost constant |

The volume of the liquid active principle to be injected is 0.5 ml. The quantities of powders have thus been determined as a function of the characteristics of the nozzle and in particular of the number of its injection channels. The diameter values given below correspond to equivalent diameters. This is because, in reality, the channels are semicylindrical longitudinal grooves whose actual diameter is 350 $\mu$m. If one likens the channels to perfect cylinders of identical cross section, then it is necessary to establish an equivalent diameter of 250 $\mu$m. The diameters mentioned below are therefore equivalent diameters.

Nozzle with 3 Channels of Diameter 250 $\mu$m
    Fast-burning powder: 30 mg
    Slow-burning powder: 30 mg.

Nozzle with 6 Channels of Diameter 250 $\mu$m
    Fast-burning powder: 31 mg
    Slow-burning powder: 25 mg.

When the number of channels decreases, the duration of the injection increases. The ratio of slow-burning powder to fast-burning powder must therefore increase in order to maintain a sufficient end-of-injection pressure. When the duration of injection increases, the total mass of powder must increase in order to limit the effect of the heat losses, but otherwise the efficacy of the thrust, in terms of % and depth of penetration, will be all the better as the number of channels is reduced, which goes toward limiting the mass of powder needed.

For this example, these quantities of powders correspond to the minimum charges permitting a percentage penetration in the region of 99% with a depth of penetration of 12 to 15 mm to be obtained, while significantly reducing the maximum pressure in the liquid of the syringe.

EXAMPLE 2

The principal characteristics of the two powders used for the second mixture are summarized in the table below:

| I - Chemical composiiton | |
|---|---|
| COMPONENTS | Fraction by mass ×100 |
| Fast-burning powder | |
| Nitrocellulose | 93.0 |
| Dinitrotoluene | 2.0 |
| Dibutylphthalate | 1.2 |
| Diphenylamine | 1.0 |
| Graphite | 0.5 |
| Residual solvent | 0.2 |
| Residual salt | 0.4 |
| Humidity | 1.2 |
| Colorant | Traces |
| Slow-burning powder | |
| Nitrocellulose | 95 |
| Additives | 5 |

| | II - Structural characteristics and parameters associated with combustion | | | | | |
|---|---|---|---|---|---|---|
| | Porosity | Combustion time (ms) | Dynamic vivacity at half combustion $(MPa \cdot s)^{-1}$ | Burning thickness (mm) | Shape of particles | Shape function |
| Fast-burning powder | YES | 0.8 | 24 | 0.2–0.5 | flake | degressive |
| Slow-burning powder | NO | 6 | 6 | 0.51 | heptatubular | progressive |

For a nozzle with 6 channels of diameter 250 μm, the quantities of powders used are:

Fast-burning powder: 42.5 mg

Slow-burning powder: 23.5 mg.

With these quantities of powders, it is possible to obtain a percentage penetration of greater than 99%.

By adapting the pyrotechnic charge to the nozzle, it is possible to obtain a pressure profile in the liquid in three phases.

The initial phase of pressure increase, which must be rapid, is obtained with a fast-burning powder.

The use of a powder having a suitable substantial burning thickness makes it possible, during the second phase, to compensate, via the gas flow rate, for the drop in pressure due to the increase in the volume of the combustion chamber and the heat losses.

Finally, the third phase which corresponds to the simple release of the combustion gas up to the end of injection does not detract from the quality of the injection. It is even desirable in order to limit the depth of penetration of the jets into the skin.

With a pyrotechnic charge thus adapted, 0.5 ml of liquid active principle is correctly injected.

What is claimed is:

1. A needleless syringe comprising, in succession, a pyrotechnic gas generator, at least one piston, a reserve of liquid active principle, and an ejection nozzle, characterized in that the pyrotechnic gas generator comprises a mixture of at least two different pyrotechnic charges.

2. The needless syringe as claimed in claim 1, characterized in that the pyrotechnic gas generator comprises a mixture of a first pyrotechnic charge and of a second pyrotechnic charge.

3. The needleless syringe as claimed in claim 2, characterized in that the first pyrotechnic charge is a gun powder and the second pyrotechnic charge is also a gun powder.

4. The needleless syringe as claimed in claim 3, characterized in that the first powder has a dynamic vivacity of greater than 8 $(Mpa.s)^{31\ 1}$.

5. The needleless syringe as claimed in claim 4, characterized in that the first powder has a burning thickness of less than or equal to 0.5 mm.

6. The needleless syringe as claimed in claim 4, characterized in that the first powder has a combustion time of less than 6 ms.

7. The needleless syringe as claimed in claim 4, characterized in that the ratio of the mass of the first powder to the total mass of the two powders is greater than 0.1.

8. The needleless syringe as claimed in claim 3, characterized in that the second powder has a dynamic vivacity which is less than 16 $(Mpa.s)^{-1}$ and which is systematically less than that of the first powder.

9. The needleless syringe as claimed in claim 8, characterized in that the second powder has a burning thickness of between 0.1 mm and 1 mm.

10. The needleless syringe as claimed in claim 8, characterized in that the second powder has a combustion time which is greater than 4 ms and which is systematic all greater than that of the first powder.

11. The needleless syringe as claimed in claim 8, characterized in that the shape function of the second powder is progressive.

12. The needless syringe as claimed in claim 8, characterized in that the shape function of the second powder is almost constant.

13. The needless syringe as claimed in claim 3, characterized in that at least one of the two powders is based on nitrocellulose, the content by mass of which is between 0.45 and 0.99.

14. The needless syringe as claimed in claim 13, characterized in that each powder based on nitrocellulose also contains nitroglycerin.

15. The needleless syringe as claimed in claim 3, characterized in that the first powder is chosen from among porous powders.

16. The needleless syringe as claimed in claim 3, characterized in that the total mass of the two powders is less than 100 mg.

17. The needleless syringe as claimed in claim 1, characterized in that the pyrotechnic gas generator comprises an initiation device, involving a percussion device and a primer.

* * * * *